United States Patent
Boudin et al.

(10) Patent No.: US 10,189,045 B2
(45) Date of Patent: Jan. 29, 2019

(54) BLACKBODY MATERIAL APPLICATION SYSTEM FOR A TURBINE

(71) Applicant: Siemens Energy, Inc., Orlando, FL (US)

(72) Inventors: Dustin C. Boudin, Belmont, NC (US); Clifford Hatcher, Jr., Orlando, FL (US); Anand A. Kulkarni, Charlotte, NC (US); Kevin Licata, Belmont, NC (US); David Letter, Deland, FL (US); Alejandro Bancalari, Casselberry, FL (US)

(73) Assignee: SIEMENS ENERGY, INC., Orlando, FL (US)

( * ) Notice: Subject to any disclaimer, the term of this patent is extended or adjusted under 35 U.S.C. 154(b) by 300 days.

(21) Appl. No.: 15/252,565

(22) Filed: Aug. 31, 2016

(65) Prior Publication Data
US 2018/0056315 A1 Mar. 1, 2018

(51) Int. Cl.
*B05B 13/06* (2006.01)
*B05C 11/10* (2006.01)
(Continued)

(52) U.S. Cl.
CPC ...... *B05B 13/0636* (2013.01); *B05B 13/0618* (2013.01); *B05C 7/02* (2013.01);
(Continued)

(58) Field of Classification Search
CPC ... B05C 7/02; B05C 11/1015; B05C 11/1018; B05B 13/0636; B05B 13/0618; C23C 4/00; G01N 21/71; G01J 5/522; G01J 5/0088; G01J 2005/0077; F01D 21/003; F05D 2270/8041; F05D 2300/224; F05D 2260/83; F05D 2220/32; F05D 2260/231; F05D 2300/611; F05D 2230/90; B05D 1/02; B05D 5/06; B05D 7/14; B05D 7/22; B05D 2202/00
(Continued)

(56) References Cited

U.S. PATENT DOCUMENTS

| 2013/0194413 A1 | 8/2013 | Hatcher |
| 2014/0044527 A1* | 2/2014 | Parkos ................ F04D 29/023 415/170.1 |

OTHER PUBLICATIONS

U.S. Appl. No. 14/684,471, filed Apr. 13, 2015, and entitled System to Prognose Gas Turbine Remaining Useful Life.
(Continued)

*Primary Examiner* — William P Fletcher, III

(57) ABSTRACT

A blackbody material application system for a turbine. The system includes a blackbody material supply and a moveable hose connected to the blackbody material supply wherein the hose sprays blackbody material onto a selected area within the turbine. The system also includes a rotatable bracket that holds the hose, wherein rotation of the bracket moves the hose toward the selected area within the turbine to enable application of the blackbody material onto the selected area. In addition, the system includes a motor for rotating the bracket and a moveable arm that holds the bracket wherein the bracket is inserted through an opening in the turbine and movement of the arm enables positioning of the bracket and hose in relative close proximity to the selected area suitable for spraying blackbody material onto the selected area.

20 Claims, 6 Drawing Sheets

(51) Int. Cl.
- *B05C 7/02* (2006.01)
- *B05D 1/02* (2006.01)
- *B05D 5/06* (2006.01)
- *B05D 7/14* (2006.01)
- *B05D 7/22* (2006.01)
- *C23C 4/00* (2016.01)
- *G01J 5/00* (2006.01)
- *G01J 5/52* (2006.01)
- *F01D 21/00* (2006.01)
- *G01N 21/71* (2006.01)

(52) U.S. Cl.
CPC ...... *B05C 11/1015* (2013.01); *B05C 11/1018* (2013.01); *B05D 1/02* (2013.01); *B05D 5/06* (2013.01); *B05D 7/14* (2013.01); *B05D 7/22* (2013.01); *C23C 4/00* (2013.01); *F01D 21/003* (2013.01); *G01J 5/0088* (2013.01); *G01J 5/522* (2013.01); *G01N 21/71* (2013.01); *B05D 2202/00* (2013.01); *F05D 2220/32* (2013.01); *F05D 2230/90* (2013.01); *F05D 2260/231* (2013.01); *F05D 2260/83* (2013.01); *F05D 2270/8041* (2013.01); *F05D 2300/224* (2013.01); *F05D 2300/611* (2013.01); *G01J 2005/0077* (2013.01)

(58) Field of Classification Search
USPC .......................................... 118/308, 317, 323
See application file for complete search history.

(56) References Cited

OTHER PUBLICATIONS

U.S. Appl. No. 15/180,364, filed Jun. 13, 2016, and entitled Flash Thermography Device for Inspecting Turbine Components.

* cited by examiner

BLACKBODY MATERIAL APPLICATION SYSTEM FOR A TURBINE

FIELD OF THE INVENTION

This invention relates to flash thermography devices used in connection with turbines, and more particularly, to a flash thermography device having a flash enclosure that includes a flash source for heating a turbine component and an infrared sensor for detecting thermal energy radiated by the turbine component wherein the flash enclosure and infrared sensor are located on a moveable arm and wherein the flash source and infrared sensor are inserted through an opening in the turbine to enable positioning in relative close proximity to a turbine component inside the turbine to enable generation of an infrared image.

BACKGROUND OF THE INVENTION

In various multistage turbomachines used for energy conversion, such as gas turbines, a fluid is used to produce rotational motion. Referring to FIGS. 1 and 2, side and perspective partial cross sectional views of an axial flow gas turbine 10 is shown. The turbine 10 includes a compressor section 12, a combustion section 14 and a turbine section 16 arranged along a horizontal center axis 18. The combustion section 14 includes a plurality of combustors 28 arrayed about the combustion section 14 that are in fluid communication with a combustion section 14 interior. Each combustor 28 includes a top hat portion 30 and a removable support housing 32. The compressor section 12 provides a compressed air flow to the combustion section 14 where the air is mixed with a fuel, such as natural gas, and ignited to create a hot working gas. The turbine section 16 includes a plurality of turbine blades 20 arranged in a plurality of rows. The hot gas expands through the turbine section 16 where it is directed across the rows of blades 20 by associated stationary vanes 22. The blades 20 are each configured as a blade assembly that is attached to a shaft that is rotatable about the center axis 18. As the hot gas passes through the turbine section 16, the gas causes the blades 20 and thus the shaft to rotate, thereby providing mechanical work. Each row of blades 20 and associated vanes 22 (i.e. collectively, "airfoils") form a stage. In particular, the turbine section 16 may include four rows of blades 20 and associated rows of vanes 22 to form four stages. The gas turbine 10 further includes an exhaust cylinder section 24 located adjacent the turbine section 16 and an outer diffuser section 26 located adjacent the exhaust cylinder section 24.

Sections of the turbine 10 that are exposed to the hot gases as the gases travel along a hot gas path in the turbine 10 may include a ceramic-based coating that serves to minimize exposure of the base metal of a component, such as an airfoil base metal, to high temperatures that may lead to oxidation of the base metal. Such a coating may be a known thermal barrier coating (TBC) that is applied onto a bond coating (BC) formed on the base metal.

A turbine 10 is typically operated for extended periods. The TBC layer or both the TBC and BC layers may undesirably deteriorate or delaminate during operation of the turbine 10. This exposes the base metal to high temperatures, which may lead to oxidation of the base metal. A turbine is inspected at periodic intervals to check for wear, damage and other undesirable conditions that may have occurred with respect to various internal components. In addition, the TBC/BC layers are inspected to determine the degree of deterioration of the TBC/BC layers (i.e. remaining thickness of the layers) and other undesirable conditions. In order to inspect components within the turbine 10, the turbine 10 is shut down and allowed to cool down, which takes a substantial amount of time. An inspection/evaluation team must then disassemble substantial portions of the turbine 10, such as an outer casing 34 and associated components, in order to gain access to a desired internal turbine component and perform an assessment or inspection of the turbine component. However, the current procedure for inspection is labor intensive, time consuming and expensive.

SUMMARY OF INVENTION

A blackbody material application system for a turbine is disclosed. The system includes a blackbody material supply and a moveable hose connected to the blackbody material supply wherein the hose sprays blackbody material onto a selected area within the turbine. The system also includes a rotatable bracket that holds the hose, wherein rotation of the bracket moves the hose toward the selected area within the turbine to enable application of the blackbody material onto the selected area. In addition, the system includes a motor for rotating the bracket and a moveable arm that holds the bracket wherein the bracket is inserted through an opening in the turbine and movement of the arm enables positioning of the bracket and hose in relative close proximity to the selected area suitable for spraying blackbody material onto the selected area.

Those skilled in the art may apply the respective features of the present invention jointly or severally in any combination or sub-combination.

BRIEF DESCRIPTION OF DRAWINGS

The teachings of the present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 1:
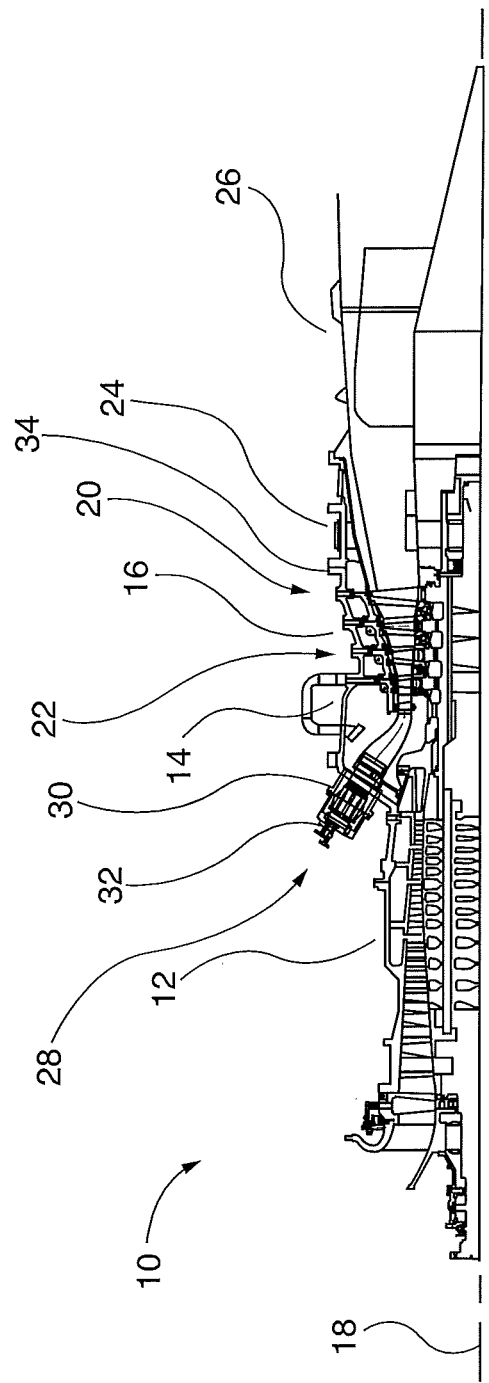
FIG. 1 is a side partial cross sectional view of an axial flow gas turbine.

Although various embodiments that incorporate the teachings of the present disclosure have been shown and described in detail herein, those skilled in the art can readily devise many other varied embodiments that still incorporate these teachings. The scope of the disclosure is not limited in its application to the exemplary embodiment details of construction and the arrangement of components set forth in the description or illustrated in the drawings. The disclosure encompasses other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

A technique for nondestructive evaluation (NDE) of turbine components includes the use of a flash thermography device. A flash thermography device may include an infrared (IR) sensor for detecting thermal energy in the infrared region of the electromagnetic spectrum. In an embodiment, the IR sensor may be an IR camera that includes a flash source although it is understood that other types of IR sensors may be used. The flash thermography device is configured to capture IR images of internal portions of a turbine to enable determination of a thickness of a BC or TBC layer formed on a component using known methods. In order to obtain an IR image of a component such as turbine vane, the flash source is energized so as to emit a light pulse that heats the vane. For example, the flash source may provide approximately 5000 to 6000 Joules of energy output to heat at least one vane. The duration of the light pulse may depend on the thickness of a BC or TBC layer on the vane that is being inspected. A portion of the thermal energy radiated by the vane is then detected by the IR sensor. The IR sensor generates IR images of the vane based on the thermal energy radiated by the vane. The length of time used for detecting the radiated thermal energy (i.e. signal collection time) is dependent upon the characteristics of the component that is being imaged. A thickness of a BC or TBC layer may then be determined from the IR images. If there is significant damage to the BC/TBC layers, the inspection/evaluation team can quickly make a decision to request maintenance in order to avoid damage of a turbine component due to loss of BC/TBC layers.

Figure 3:
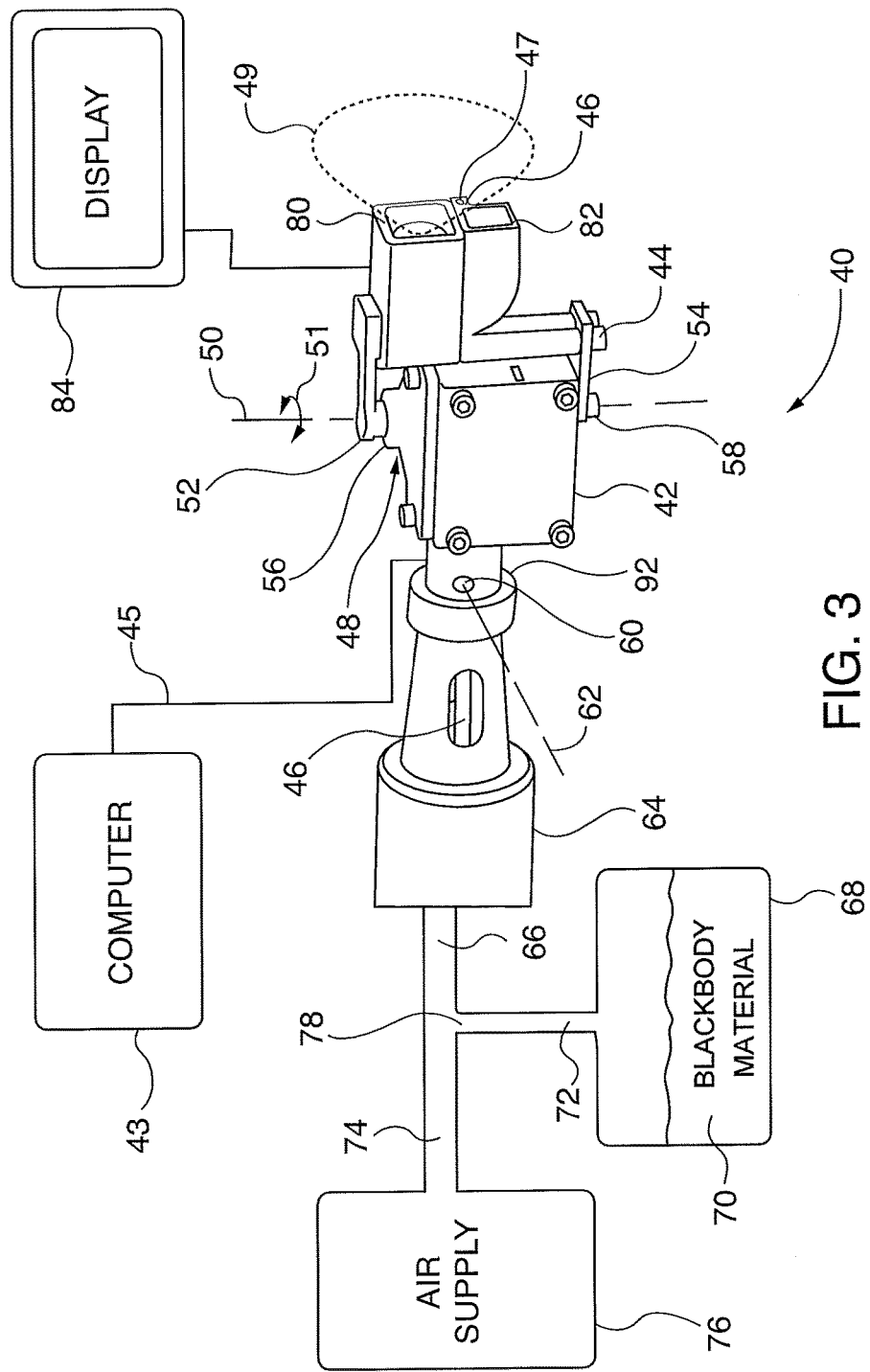
FIG. 3 depicts a blackbody material application system for a turbine in accordance with an embodiment of the invention.

It is desirable to increase an emissivity of thermal energy emitted by internal portions of a turbine or a turbine component being imaged so as to increase an amount of data detected by the IR sensor and thus enhance the IR images that are ultimately generated. Referring to FIG. 3, a blackbody material application system 40 for a turbine 10 is shown. The system 40 includes a servomotor 42 and a rotatable bracket element 44 having a flexible tube or hose 46 that emits or sprays a material 70 having blackbody properties that increase an emissivity of thermal energy emitted by internal portions of a turbine or a turbine component being imaged. In particular, the blackbody material 70 may be any coating that renders a TBC layer opaque. As a preferred option, the blackbody material 70 may be graphite or a graphite based paint. The servomotor 42 includes an output shaft 48 that rotates about a vertical axis 50. The bracket 44 includes upper 52 and lower 54 attachment elements that are attached to upper 56 and lower 58 ends of the output shaft 48, respectively, to enable rotation of the bracket 44 about the vertical axis 50 (see arrow 51). Rotation of the bracket 44 causes corresponding movement of the hose 46. In operation, the bracket 44 is rotated to move the hose 46 to a desired position suitable for spraying the blackbody material 70 onto a selected area within the turbine 10. In an embodiment, the blackbody material 70 is sprayed from a hose end 47 of the hose 46 in a substantially cone shaped pattern. Alternatively, the blackbody material 70 may be sprayed from the hose 46 during rotation of the bracket 44 to provide a sweeping motion in order to spray the blackbody material 70 onto a relatively wider area within the turbine 10. It is understood that the output shaft 48 may be positioned in other orientations. In addition, the system 40 may include a horizontal pivot 60 to enable rotation of the system 40 about a horizontal axis 62 in addition to rotation about the vertical axis 50.

The hose 46 extends through an arm 64 and is connected to a main supply line 66. A container 68 for holding blackbody material 70 is connected to the main supply line 66 by a blackbody material supply line 72. An air channel 74 is connected to an air supply 76, blackbody material supply line 72 and the main supply line 66. The main supply line 66, air channel 74, air supply 76, blackbody material supply line 72, blackbody material 70 and container 68 form an air jet sprayer arrangement for spraying blackbody material although it is understood that other types of sprayer arrangements may be used. Further, gases other than air may be used. Air from the air supply 76 moves through the air channel 74 past a top 78 of the blackbody material supply line 72. This causes a vacuum that draws the blackbody material 70 through the blackbody material supply line 72 and into main supply line 66 such that blackbody material 70 ultimately exits the hose end 47 as a spray.

In addition, the bracket 44 includes an imaging device such as a video camera 80 and associated lamp 82. The camera 80 is coupled to a display 84 that enables an operator to observe components, systems and surfaces located within the turbine 10 that are within a field of view of the camera 80. The lamp 82 illuminates internal portions of the turbine 10 to assist in viewing the interior of the turbine 10 and navigating the system 40 to a desired position within the turbine 10 suitable for spraying blackbody material onto a selected area of interest within the turbine 10. Operation of the system 40 is controlled by computer 43 that is connected to the system 43 by electrical connection 45.

Figure 4:
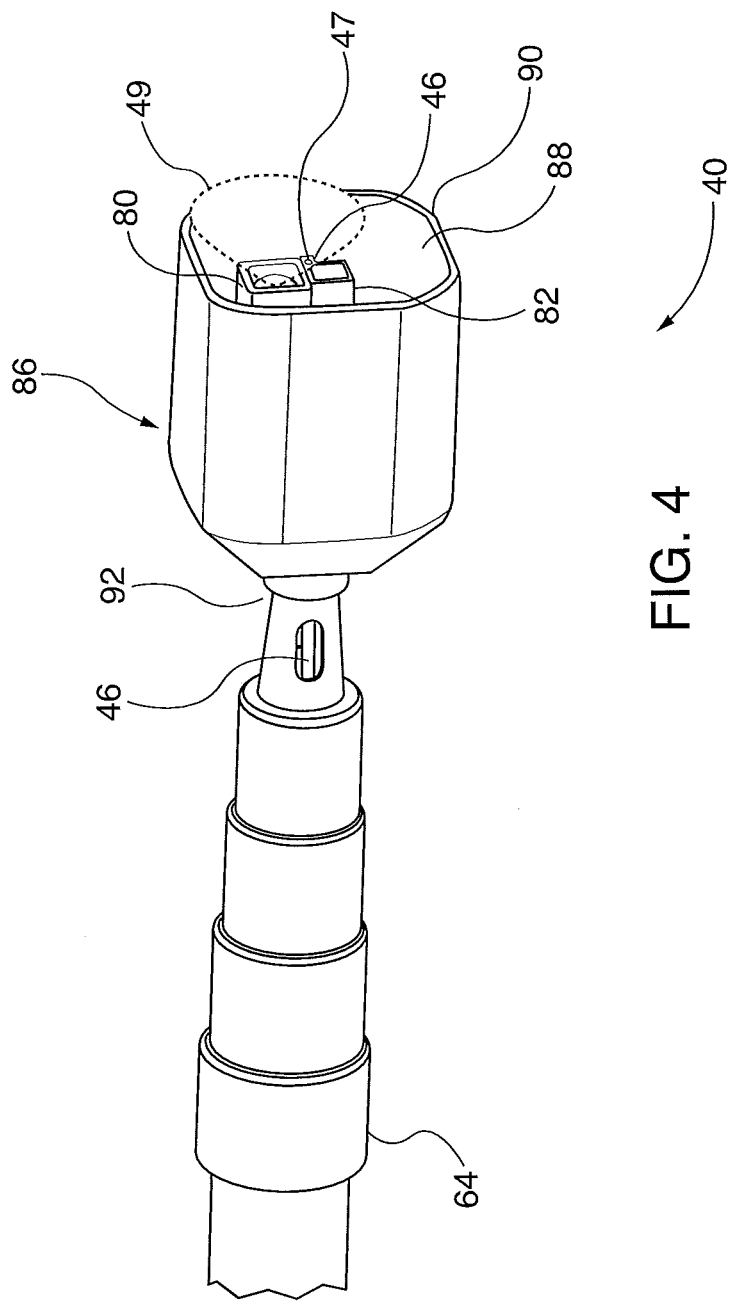
FIG. 4 depicts the blackbody material application system further including an enclosure for housing portions of a servomotor and a bracket.

Referring to FIG. 4, the system 40 further includes an enclosure 86 for housing portions of the servomotor 42 and bracket 44. The enclosure includes an opening 88 on an end 90 that exposes the camera 80, lamp 82 and hose end 47. The enclosure 86 serves to protect the servomotor 42, bracket 44 and associated components from blackbody material overspray. The system 40 is mounted to an end 92 of the arm 64. In an embodiment, the arm 64 is an extendable or telescopic arm 64. In use, an operator is able to insert the device 40 and arm 64 through an opening in the turbine 10 and move the arm by extending, retracting and/or orienting the arm 64 as desired. This enables navigation and positioning of the system 40 in relative close proximity to a selected area of interest within the turbine 10, such as the row 1 vanes, that is suitable for spraying blackbody material onto the selected area. With respect to optical inspection systems, the disclosure of U.S. Patent Publication No. 2013/0194413 A1, application Ser. No. 13/362,417, published on Aug. 1, 2013, entitled SYSTEM AND METHOD FOR AUTOMATED OPTICAL INSPECTION OF INDUSTRIAL GAS TURBINES AND OTHER POWER GENERATION MACHINERY to Hatcher et al. is hereby incorporated by reference in its entirety. In addition, the disclosure of application Ser. No. 14/684,471, filed on Apr. 13, 2015, entitled SYSTEM TO PROGNOSE GAS TURBINE REMAINING USEFUL LIFE to Iyer et al. is also hereby incorporated by reference in its entirety.

Figure 2:
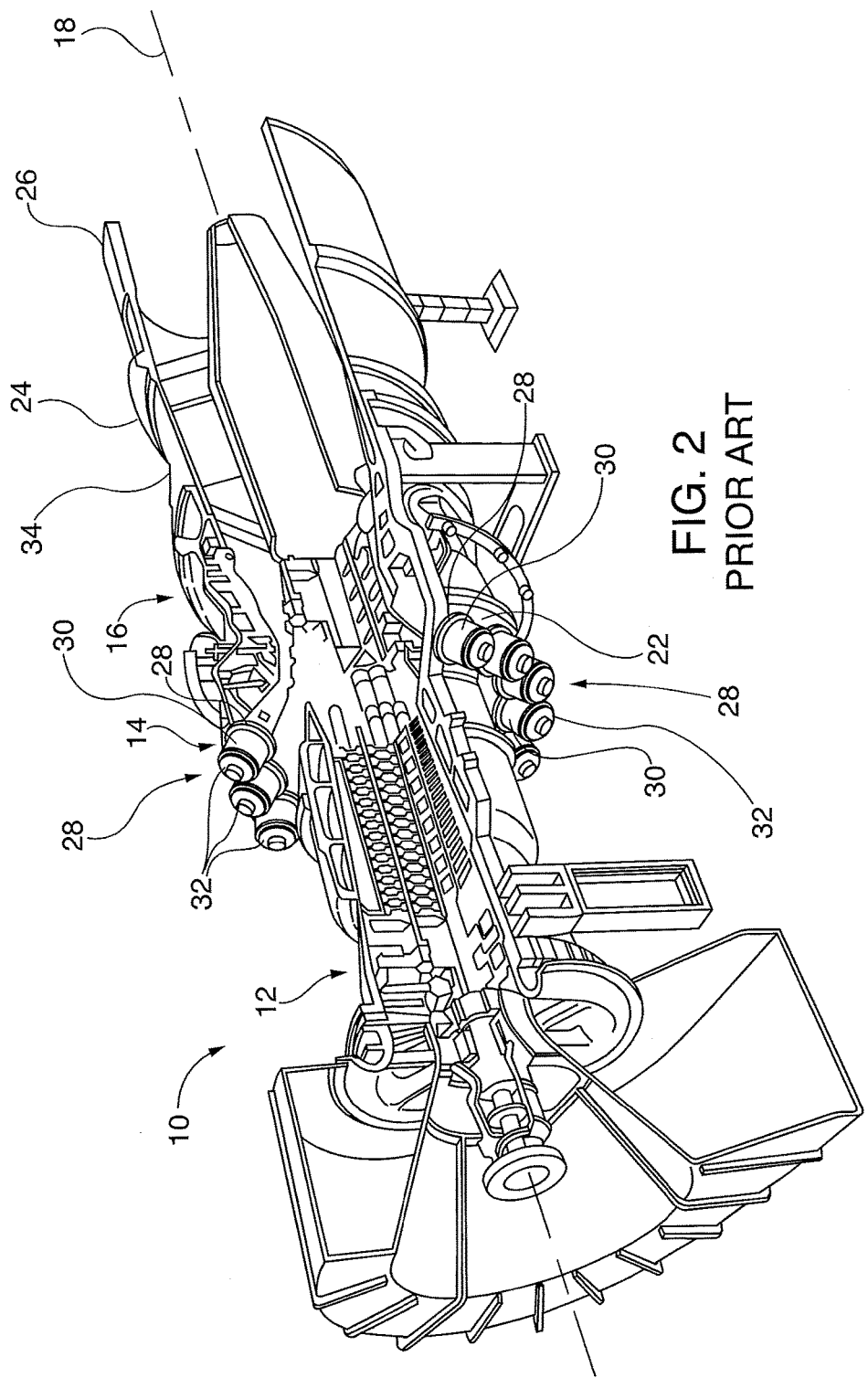
FIG. 2 is a perspective partial cross sectional view of an axial flow gas turbine.
Figure 5:
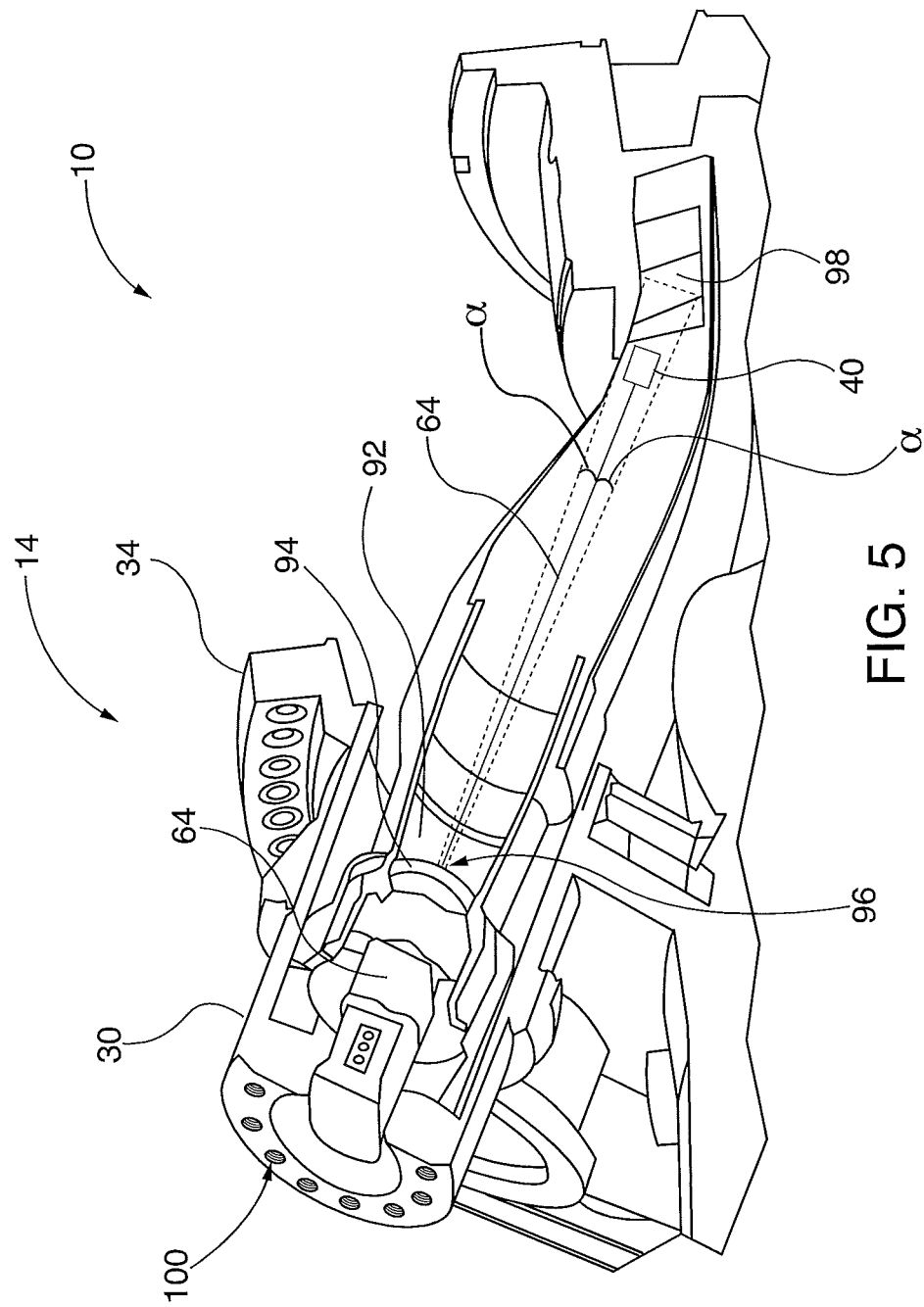
FIG. 5 is a partial cross sectional view of the turbine wherein the system and an arm are shown inserted through an opening the turbine in order to position the system in a suitable position for spraying a blackbody material onto a selected area within the turbine.

The system 40 and arm 64 are sized to enable insertion of the system 40 and arm 64 through an opening in the turbine 10. In an embodiment, the system 40 and arm 64 may be inserted through an approximately 4.5 inch size opening available in a large turbine. As previously described in relation to FIGS. 1 and 2, the combustion section 14 includes a plurality of combustors 28 arrayed about the combustion section 14 that are in fluid communication with a combustion section 14 interior. Each combustor 28 includes a top hat portion 30 and a removable support housing 32. FIG. 5 is a partial cross sectional view of the turbine wherein the system 40 and arm 64 are shown inserted through an opening the turbine in order to position the system 40 in a suitable position for spraying blackbody material onto a selected area within the turbine. In FIG. 5, a selected support housing 32 (see FIGS. 1 and 2) is shown removed. Removal of the support housing 32 provides access to an opening 92 in the turbine 10. In accordance with the invention, the system 40 and arm 64 are sized to enable insertion of the system 40 and arm 64 through the opening 92. For example, the system 40 and arm 64 may be inserted through an opening in a pilot cone 94 of a combustor basket portion 96. The arm 64 may then be extended, retracted and/or oriented at an angle α as desired to enable positioning of the system 40 in relative close proximity to an item of interest in the turbine 10, such as the row 1 vanes 98. Thus, the system 40 may be navigated to a desired position within the turbine 10 that is suitable for spraying blackbody material onto a selected area of interest within the turbine 10. The arm 64 may be hand held and moved by an operator. Alternatively, the arm 64 may be affixed to a mounting fixture using preexisting apertures 100 used for securing a support housing 32. It is understood that other openings in the turbine 10 may be used to navigate the system 40 to a desired position within the turbine 10 suitable for spraying blackbody material onto a selected area of interest within the turbine 10.

Figure 6:
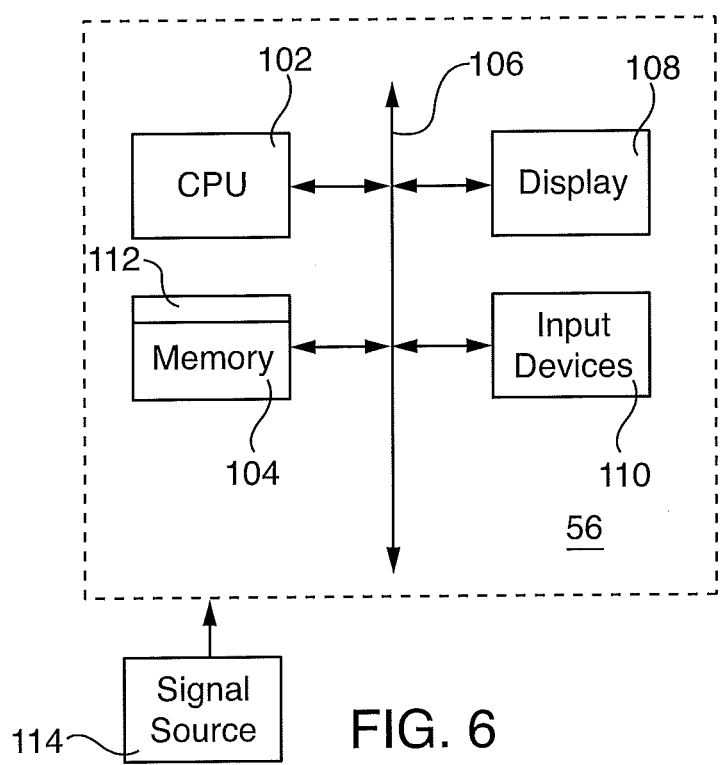
FIG. 6 is a high-level block diagram of a computer.

Referring back to FIG. 3, the system 40 is communicatively coupled to the computer 43 by electrical connection 45 or a wireless connection. The computer 43 includes software and drivers for controlling operation of the system 40 and associated components and/or systems. The computer 43 may use well-known computer processors, memory units, storage devices, computer software, and other components. A high-level block diagram of such a computer is illustrated in FIG. 6. Computer 43 may include a central processing unit (CPU) 102, a memory 104 and an input/output (I/O) interface 106. The computer 43 is generally coupled through the I/O interface 106 to a display 108 for visualization and various input devices 110 that enable user interaction with the computer 43 such as a keyboard, keypad, touchpad, touchscreen, mouse, speakers, buttons or any combination thereof. Support circuits may include circuits such as cache, power supplies, clock circuits, and a communications bus. The memory 104 may include random access memory (RAM), read only memory (ROM), disk drive, tape drive, etc., or a combination thereof. Embodiments of the present disclosure may be implemented as a routine 112 that is stored in memory 104 and executed by the CPU 102 to process the signal from a signal source 114. As such, the computer 43 is a general purpose computer system that becomes a specific purpose computer system when executing the routine 112. The computer 43 can communicate with one or more networks such as a local area network (LAN), a general wide area network (WAN), and/or a public network (e.g., the Internet) via a network adapter. One skilled in the art will recognize that an implementation of an actual computer could contain other components as well, and that FIG. 6 is a high level representation of some of the components of such a computer for illustrative purposes.

The computer 43 also includes an operating system and micro-instruction code. The various processes and functions described herein may either be part of the micro-instruction code or part of the application program (or a combination thereof) which is executed via the operating system. In addition, various other peripheral devices may be connected to the computer platform such as an additional data storage device and a printing device. Examples of well-known computing systems, environments, and/or configurations that may be suitable for use with computer 56 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like. In some examples, the computer 43 is disposed within and considered a part of system 40 or display 108. In still other examples, the computer 43 may be co-located in both system 40 and display 86.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A blackbody material application system for a turbine, comprising:
    a blackbody material supply;
    a moveable hose connected to the blackbody material supply wherein the hose sprays blackbody material onto a selected area within the turbine;
    a rotatable bracket that holds the hose, wherein rotation of the bracket moves the hose toward the selected area within the turbine to enable application of the blackbody material onto the selected area; and
    a motor for rotating the bracket.

2. The system according to claim 1, wherein the bracket is rotatable about a vertical axis.

3. The system according to claim 1, wherein the bracket further includes a camera and a lamp to enable viewing of components and surfaces located within the turbine to assist in positioning the bracket and hose relative to the selected area.

4. The system according to claim 1, wherein the blackbody material is a graphite based paint.

5. The system according to claim 4, wherein the blackbody material supply includes an air supply for drawing the graphite into an air channel to form a spray.

6. The system according to claim 1, wherein the blackbody material is sprayed in a substantially cone shaped pattern.

7. The system according to claim 1, wherein the system is located within an enclosure that protects the system from blackbody material overspray.

8. The system according to claim 1, wherein the selected area includes a thermal barrier coating and/or a bond coating.

9. A blackbody material application system for a turbine, comprising:
   a blackbody material supply;
   a moveable hose connected to the blackbody material supply wherein the hose sprays blackbody material onto a selected area within the turbine;
   a rotatable bracket that holds the hose, wherein rotation of the bracket moves the hose toward the selected area within the turbine to enable application of the blackbody material onto the selected area;
   a motor for rotating the bracket; and
   a moveable arm that holds the bracket wherein the bracket is inserted through an opening in the turbine and movement of the arm enables positioning of the bracket and hose suitable for spraying blackbody material onto the selected area.

10. The system according to claim 9, wherein the bracket is rotatable about a vertical axis.

11. The system according to claim 9, wherein the bracket further includes a camera and a lamp to enable viewing of components and surfaces located within the turbine to assist in positioning of the bracket and hose relative to the selected area.

12. The system according to claim 9, wherein the blackbody material is a graphite based paint.

13. The system according to claim 12, wherein the blackbody material supply includes an air supply for drawing the graphite into an air channel to form a spray.

14. The system according to claim 12, wherein the blackbody material is sprayed in a substantially cone shaped pattern.

15. The system according to claim 9, wherein the system is located within an enclosure that protects the system from blackbody material overspray.

16. The device according to claim 9, wherein the selected area includes a thermal barrier coating and/or a bond coating.

17. A method for applying blackbody material onto a selected area inside a turbine, comprising:
   providing a blackbody material supply;
   providing a moveable hose connected to the blackbody material wherein the hose sprays blackbody material onto the selected area within the turbine;
   providing a rotatable bracket that holds the hose, wherein rotation of the bracket moves the hose toward the selected area within the turbine to enable application of the blackbody material onto the selected area;
   providing a motor for rotating the bracket; and
   providing a moveable arm that positions the bracket and hose inside the turbine suitable for spraying blackbody material onto the selected area.

18. The method according to claim 17, wherein the bracket is rotatable about a vertical axis.

19. The method according to claim 17, wherein the bracket further includes a camera and a lamp to enable viewing of components and surfaces located within the turbine to assist in positioning of the bracket and hose relative to the selected area.

20. The method according to claim 17, wherein the blackbody material is a graphite based paint.

* * * * *